US007030742B2

(12) United States Patent
Treadway

(10) Patent No.: US 7,030,742 B2
(45) Date of Patent: Apr. 18, 2006

(54) DUAL CHANNEL AIR/FUEL RATIO GAUGE

(75) Inventor: Matthew Treadway, Buena Park, CA (US)

(73) Assignee: Innova Electronics Corp., Fountain Valley, CA (US)

( * ) Notice: Subject to any disclaimer, the term of this patent is extended or adjusted under 35 U.S.C. 154(b) by 217 days.

(21) Appl. No.: 10/727,249

(22) Filed: Dec. 3, 2003

(65) Prior Publication Data

US 2005/0122226 A1  Jun. 9, 2005

(51) Int. Cl.
- *B60Q 1/00* (2006.01)
- *G01N 7/00* (2006.01)
- *F02D 41/22* (2006.01)

(52) U.S. Cl. ............... 340/439; 340/632; 73/23.32; 123/673

(58) Field of Classification Search ........... 340/439, 340/632; 73/23.32; 60/276; 123/672
See application file for complete search history.

(56) References Cited

U.S. PATENT DOCUMENTS

| 4,696,359 A | * | 9/1987 | Glibbery | 177/211 |
| 5,363,091 A | * | 11/1994 | Kotwicki et al. | 340/439 |
| 5,519,397 A | * | 5/1996 | Chapotot et al. | 341/155 |
| 5,668,542 A | * | 9/1997 | Wright | 340/971 |
| 5,952,555 A | * | 9/1999 | Mobius | 73/23.32 |
| 6,279,377 B1 | * | 8/2001 | Cao | 73/23.31 |
| 6,371,097 B1 | * | 4/2002 | Rossi | 123/691 |
| 6,923,902 B1 | * | 8/2005 | Ando et al. | 205/781 |

FOREIGN PATENT DOCUMENTS

| FR | 192500 A | * | 8/1986 |
| JP | 11281513 A | * | 10/1999 |
| US | EP-634185 A2 | * | 1/1995 |

* cited by examiner

Primary Examiner—Jeffery Hofsass
Assistant Examiner—Anne V. Lai
(74) Attorney, Agent, or Firm—Stetina Brunda Garred & Brucekr

(57) ABSTRACT

There is provided an air/fuel ratio gauge for monitoring an engine exhaust mixture of an engine having a plurality of oxygen sensors. The gauge of the present invention comprises a gauge housing. A gauge controller is disposed within the gauge housing and is electrically communicated with the engine. The gauge controller is operative to receive a sensor voltage output signal from each of the plurality of oxygen sensors. Furthermore, at least two gauge displays are each electrically communicated with the gauge controller and an associated oxygen sensor. Each gauge display is operative to independently display sensor information representative of the associated oxygen sensor operation.

20 Claims, 3 Drawing Sheets

DUAL CHANNEL AIR/FUEL RATIO GAUGE

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

The present invention relates generally to air/fuel ratio gauges, and more particularly to an improved air/fuel ratio gauge featuring a gauge display which provides separate sets of visual indicators adapted to operate independent of each other when simultaneously monitoring an exhaust mixture of a single or dual exhaust system.

Air/fuel ratio gauges are typically used to monitor exhaust mixtures, that is, the ratio of air to unburned fuel in exhaust systems of automobiles. These gauges are essentially voltmeters that display the voltage outputs of oxygen sensors in order to determine the richness (i.e., less air, more fuel) or leanness (i.e., more air, less fuel) of the exhaust mixtures. Ideally, the exhaust mixtures should be at stoichiometric which is the perfect ratio of air and fuel.

The exhaust mixture of a typical automobile runs back and forth between rich and lean. For instance, when the automobile is accelerated, more fuel is injected into its engine to keep the exhaust mixture rich. This gives the automobile maximum power for acceleration. Under deacceleration, however, the engine leans out the exhaust mixture which has the obvious effect of conserving fuel.

As the automobiles frequently alternate between rich and lean exhaust mixtures, it is important to monitor such conditions to avoid any serious damages to their engines. For example, a vacuum leak or a drop in fuel pressure could potentially damage the engine of the automobile assuming that the ratio between air and fuel is extremely lean. By monitoring the exhaust mixture conditions, problems such as vacuum leaks or low fuel pressures can be revealed and repaired before any serious damage to the automobile's engine occurs.

The air/fuel ratio gauge is a good indicator of potentially serious damages to the engine of an automobile. A typical air/fuel ratio gauge is incorporated near a driver's section of the automobile and electrically wired to an oxygen sensor attached about the side of the engine. By establishing such electrical connection, the oxygen sensor can measure the presence of oxygen in the exhaust and provide its measurements to the air/fuel ratio gauge in the form of voltage outputs. The air/fuel gauge then translates these voltage outputs into visual indicia easily recognizable by the driver and displays the same on its visual display.

Although the conventional air/fuel ratio gauges may be satisfactory for a single exhaust system, they cannot however account for a dual exhaust system. This is because dual exhaust systems typically employ the use of two oxygen sensors for each of the two exhausts. Because the conventional gauges are designed to be used with one oxygen sensor at a time, the exhaust mixture measurement accounts for only one of the exhausts. The driver must therefore rely on the exhaust mixture ratio of that exhaust as an indication of the status of the other exhaust. As such, the current gauges in the marketplace cannot provide complete assessments as to the exhaust mixture ratios when it comes to automobiles with dual exhaust systems.

Even though two air/fuel ratio gauges may theoretically be applied to dual exhaust automobiles, it would be extremely impractical to take such course of action. First, the cost of doing so would obviously be more expensive as opposed to implementing the use of only one gauge. Further, the incorporation of an additional air/fuel ratio gauge into the automobile may undesirably complicate the interior aesthetics thereof since the space is usually limited within the automobile. More importantly, however, the use of multiple gauges may significantly jeopardize the safety of the driver, passengers and others as the driver can easily be distracted on the road due to separate visual displays which must be read. Understandably, this can compromise the driver's focus on the road.

Thus, there has long been a need in the industry, and in the automobile industry in particular, for a single air/fuel ratio gauge that can operate with both single and dual exhaust systems in order to assess the ratio between air and fuel in their exhaust mixtures. More specifically, there is a need for an air/fuel ratio gauge which can perform such assessments in all the exhausts of the exhaust system and display the same to its user in an easy-to-read manner through the use of a single visual display.

The present invention addresses and overcomes the above-described deficiencies of prior art air/fuel ratio gauges by providing a single air/fuel ratio gauge which is adapted to monitor the exhaust mixtures of both single exhaust systems and dual exhaust systems. Furthermore, such air/fuel ratio gauge additionally features a single gauge display that provides separate sets of independently operating visual indicators each directed to their respective exhausts so as to provide all exhaust mixture assessments on one visual display. In this respect, not only does the present invention mitigate the need for multiple air/fuel gauges, but it more importantly allows its users to concentrate on their primary tasks (e.g., driving) while receiving complete exhaust mixture assessments for all the exhausts involved.

BRIEF SUMMARY OF THE INVENTION

In accordance with the present invention, there is provided an air/fuel ratio gauge for monitoring an engine exhaust mixture of an engine having at least one oxygen sensor. The gauge of the present invention comprises a gauge housing. A gauge controller is disposed within the gauge housing and is electrically communicated with the engine. The gauge controller is operative to receive a sensor voltage output signal from each of the plurality of oxygen sensors. Furthermore, at least two gauge displays are each electrically communicated with the gauge controller and an associated oxygen sensor. Each gauge display is operative to independently display sensor information representative of the associated oxygen sensor operation.

More specifically, the gauge housing has at least two sensor terminals operative to communicate the sensor voltage output signals to the gauge controller. Each of the gauge displays are operative to display the associated sensor information independent of the other gauge display based upon the sensor voltage output signal received from the associated sensor.

In accordance with the present invention, the sensor voltage output signal ranges from about 0 volt to about 1 volt. The sensor voltage output signal in a range from about 0 volt to about 0.3 volt represents a substantially greater amount of air than fuel in the engine exhaust mixture. Further, the sensor voltage output signal in a range from about 0.301 volt to about 0.7 volt represents a substantially equal amount of air and fuel in the engine exhaust mixture. The sensor voltage output signal in a range from about 0.701 volt to about 1.0 volt represents a substantially greater amount of fuel than air in the engine exhaust mixture.

In the present invention, the gauge displays preferably include light emitting diodes. Moreover, the gauge controller preferably includes at least one auto zeroing circuit operative to zero the gauge displays at zero levels. Further preferably, the gauge controller includes at least one buffering circuit for attenuating transient oscillation of the sensor information displayed by the gauge display.

BRIEF DESCRIPTION OF THE DRAWINGS

These as well as other features of the present invention will become more apparent upon reference to the drawings wherein.

DETAILED DESCRIPTION OF THE INVENTION

Figure 1:
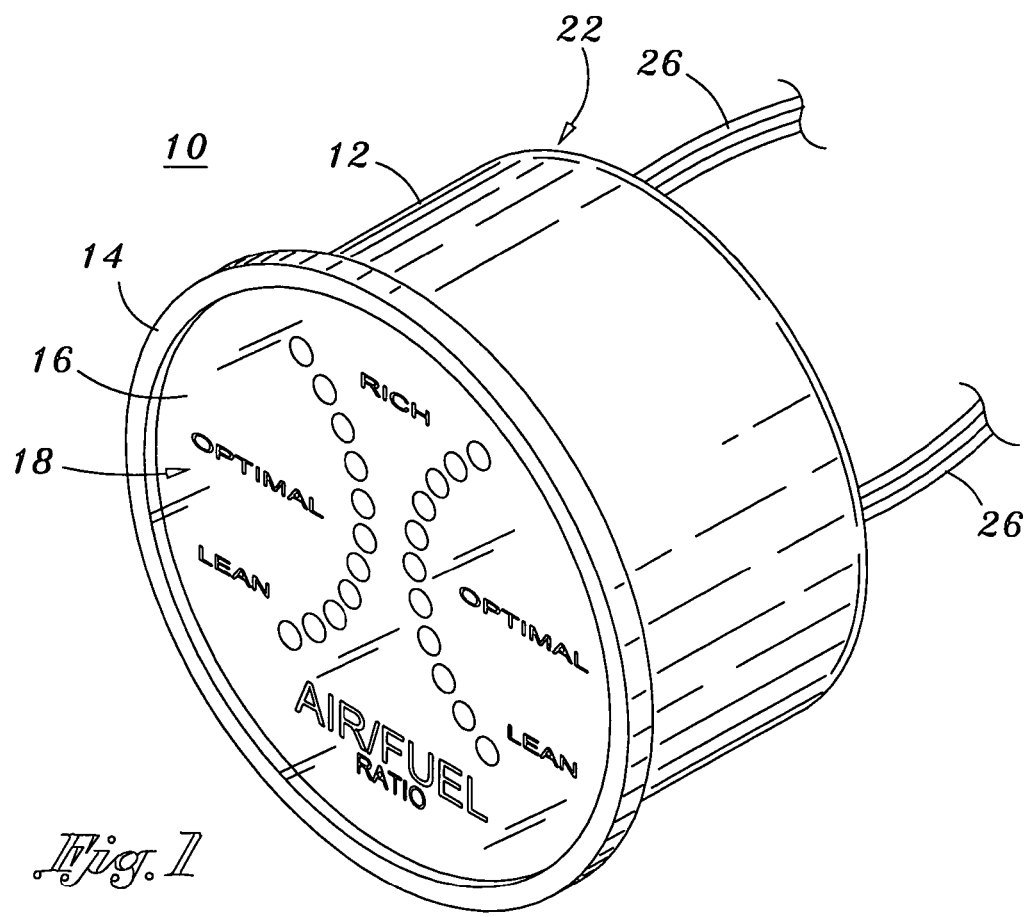
FIG. 1 is a perspective view of an air/fuel ratio gauge constructed in accordance with a preferred embodiment of the present invention and including two electrical connections which may collectively connect to one oxygen sensor or separately connect to two oxygen sensors.

Referring now to the drawings wherein the showings are for purposes of illustrating preferred embodiments of the present invention only, and not for purposes of limiting the same, FIG. 1 perspectively illustrates an air/fuel ratio gauge 10 constructed in accordance with a preferred embodiment of the present invention. The air/fuel ratio gauge 10 is adapted to be installed within a vehicle (not shown) such as an automobile and assess the contents of its exhaust mixtures. The gauge 10 of the present invention may be installed within the vehicle during manufacture or retrofitted after the manufacture of the vehicle. It should be recognized herein that the application of the present invention's gauge 10 is in no way limited to automobiles but may extend to other types of vehicles and/or machines such as aircrafts, ships, generators and the like.

Figure 2:
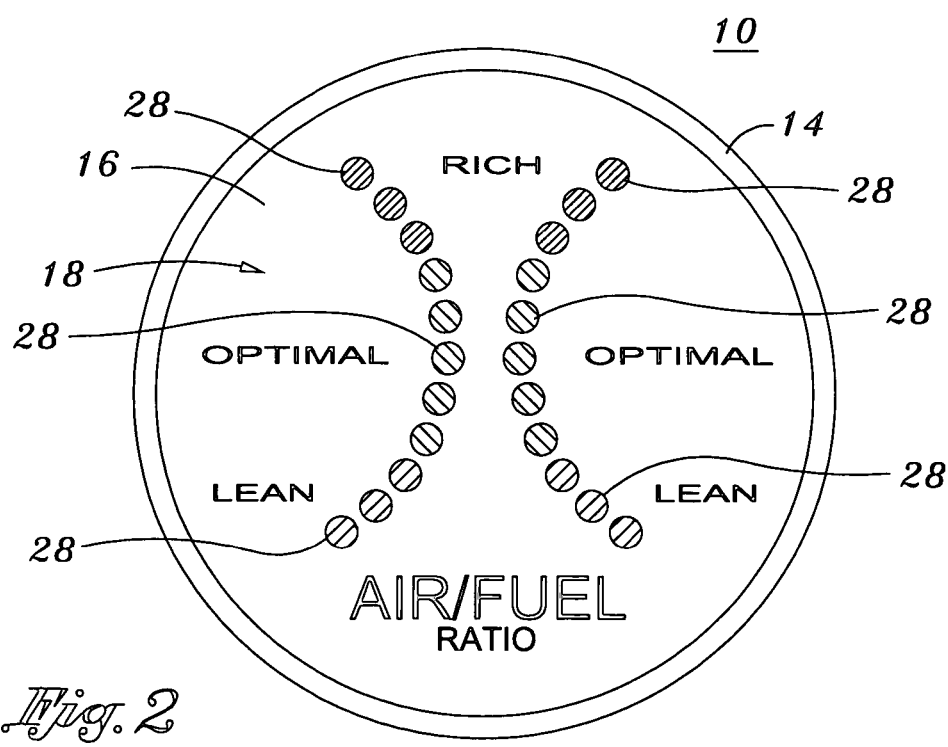
FIG. 2 is a front view of the air/fuel ratio gauge of FIG. 1 and illustrating its gauge display which features two gauge displays configured to operate independent of each other.

Referring more particularly to FIGS. 1 and 2, the air/fuel ratio gauge 10 includes a gauge housing 12 which is designed to be engaged within the vehicle. Preferably, the gauge housing 12 is provided about the driver's section of the vehicle so that the gauge 10 may be easily and conveniently read while driving. It is preferably fabricated from a rigid material such as plastic or metal so as to provide optimal protective shelling to any electrical or mechanical components placed therewithin.

The gauge housing 12 has a front housing surface 14 which is designed to face generally towards the driver upon its installation and use. The front housing surface 14 includes a transparent display face 16 which allows a gauge controller 18 to be shown therethrough. In order to afford such transparency, the transparent display face 16 may be constructed from glass or clear plastic. Simply put, the gauge controller 18, which functions to provide continuous exhaust mixture assessments, can be visible from the front housing surface 14 through its display face 16. Optionally, the display face 16 may be tinted using a conventional tinting material so as to be effectively utilized even when sunlight is radiated thereupon during daytime. Of course, such tinting should not darken the display face 16 to the degree in which any visual indicia provided by the gauge controller 18 is not able to be seen therethrough.

As briefly mentioned above, a gauge controller 18 operative to provide visual representations of the exhaust mixture assessments is disposed within the gauge housing 12. The gauge controller 18 is communicated to the engine of the vehicle. More particularly, it is communicated to one oxygen sensor 20 generally located on one side of the engine (for single exhaust system, or two oxygen sensors 20 generally located on opposite sides of the engine (for dual exhaust system). This aspect of the invention will be emphasized shortly below. It should be noted that, although electrical wiring connection between the gauge controller 18 and the oxygen sensor(s) 20 is preferred, a wireless connection may be an alternative connectivity implementation.

Moreover, various types of oxygen sensors 20 may be utilized in conjunction with the gauge 10 of the present invention. However, –1 volt oxygen sensors 20 are preferred over the others. For vehicles that do not have or use 0–1 volt oxygen sensors 20, a generic oxygen sensor may be installed for use with the air/fuel ratio gauge 10 of the present invention. Even with the generic oxygen sensor, the gauge 10 of the present invention can operate on any vehicle that runs on gasoline carbureted and/or fuel injected. But, a weld-in bung/fitting should be installed before the catalyst is sourced which may be easily done for a nominal fee in any local muffler shops.

Referring now to FIG. 1 only, the gauge housing 12 has a rear housing surface 22 which is adapted to communicate the gauge controller 18 with one or more oxygen sensors 20 of the engine. More particularly, the rear housing surface 22 includes two sensor terminals 24 that have electrical wires 26 leading to the oxygen sensor(s) 20 for connection thereto. This effectively places the gauge controller 18 and the oxygen sensor(s) 20 in wired communication with each other. By such electrical connection, the gauge controller 18 can receive exhaust mixture assessments in the form of voltage outputs from one or more oxygen sensors 20 of the vehicle's engine.

Figure 4:
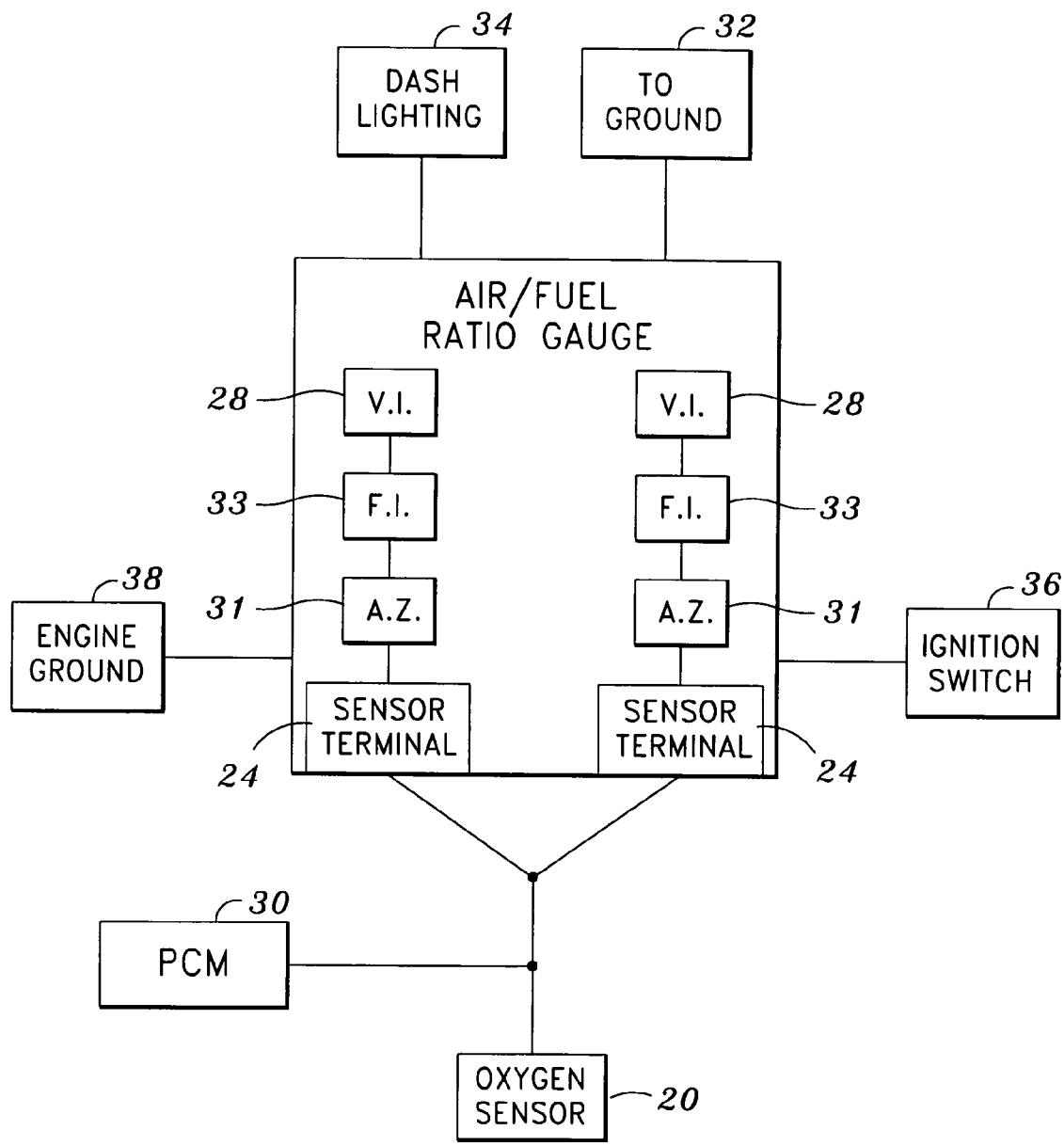
FIG. 4 is a schematic diagram of the air/fuel ratio gauge of FIG. 1 and illustrating its electrical connection to one oxygen sensor typically employed in single exhaust systems.

As illustrated in FIGS. 1, 2 and 4, the gauge controller 18 includes two gauge displays 28 thereon. The two gauge displays 28 correspond to a respective one of the sensor terminals 24. More specifically, gauge displays 28 are placed in electrical communication with their respective sensor terminals 24, so that they may operate and function in complete independence from each other. In this regard, each gauge display 28 is configured to project out its own visual indicia representative of the exhaust mixture assessments separate and apart from the other, based upon the voltage output received from the oxygen sensor(s) 20 through its respective sensor terminal 24. Although they are required to independently operate without each other's intervention, it is preferred that their operations are synchronized so that both projects out a display simultaneously. This simulates the actions of two separate gauges operating at the same time, but is done so within the workings of only one single air/fuel ratio gauge 10.

FIG. 4 specifically shows the electrical communication of the present invention's ratio gauge 10 for a vehicle with single exhaust system having only one oxygen sensor 20. In this event, the electrical wires 26 extending from the sensor terminals 24 and leading to the oxygen sensor 20 are first connected together outside the gauge housing 12 prior to being wired to the oxygen sensor 20. In this respect, the two gauge displays 28 may display separate mixture assessing visual indicia based upon the same voltage output received from the oxygen sensor 20 of the engine. In this specific embodiment of the present invention, each gauge display 28 would operate independently to put out a substantially identical reading as the other set since the same voltage outputs reflective of the exhaust mixture assessments are the same.

Figure 3:
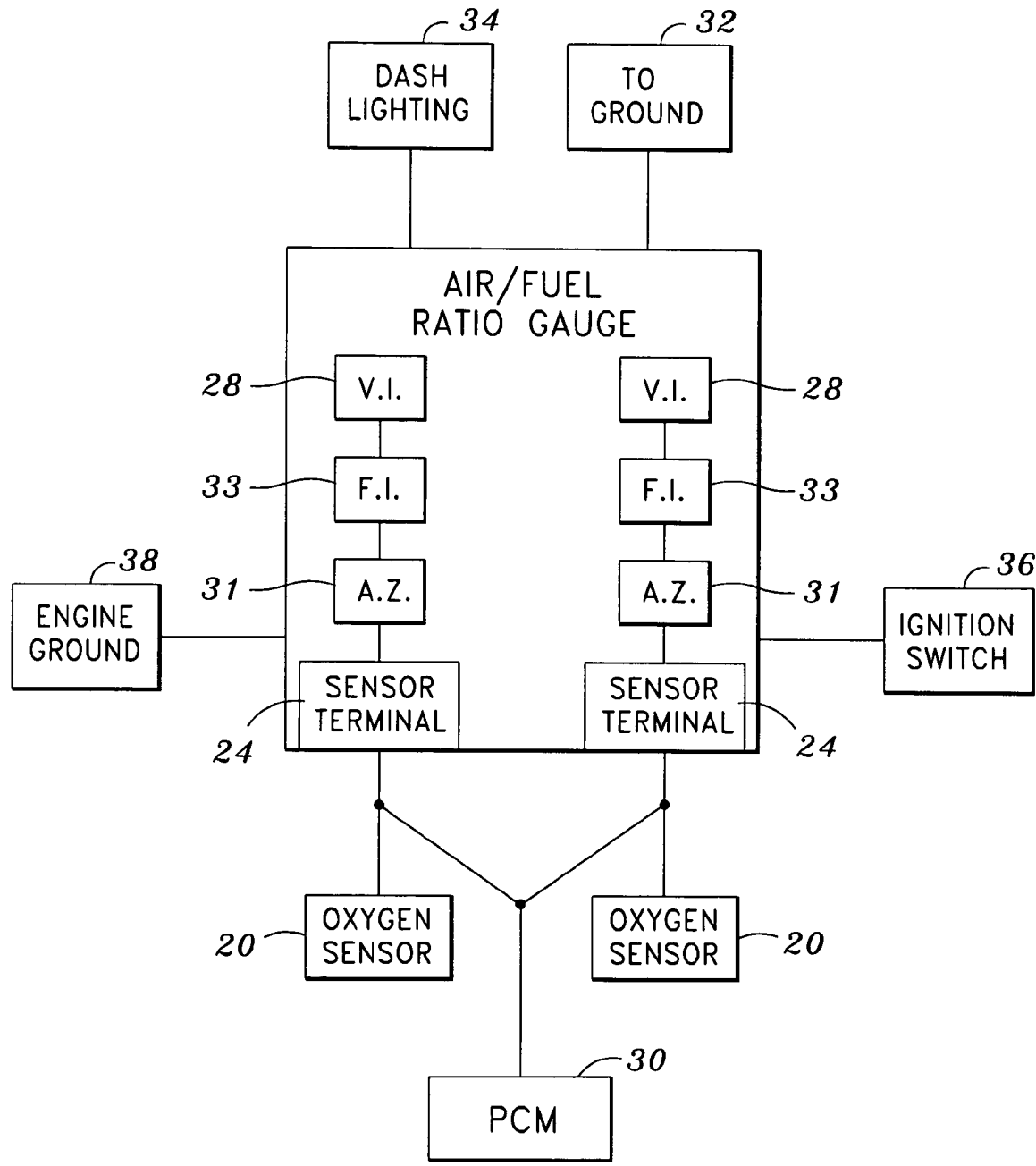
FIG. 3 is a schematic diagram of the air/fuel ratio gauge of FIG. 1 and illustrating its electrical connection to two separate oxygen sensors typically employed in dual exhaust systems.

Referring now to FIG. 3, the electrical connection of the air/fuel ratio gauge 10 for a vehicle with dual exhaust system having two oxygen sensors 20 is somewhat different than above. For dual exhaust systems, the electrical wires 26 extending from the sensor terminals 24 are not wired together outside the gauge housing 12. Rather, they are led and connected directly to their respective oxygen sensors 20. This allows the gauge controller 18 to receive two separate voltage outputs from the oxygen sensors 20, each output being representative of the exhaust mixture from a separate exhaust.

As such, the two gauge displays 28 each display a separate visual measurement independent of each other, which permits the driver to know the status of the exhaust mixtures of each exhaust. In other words, each of the gauge displays 28 provides exhaust mixture readings separate and apart from the other, based solely upon the voltage outputs from its associated oxygen sensor 20. Consequently, the air/fuel ratio gauge 10 of the present invention can optimally assess the exhaust mixture content of each exhaust in a dual exhaust system rather than estimating one based upon the assessment of only one exhaust. This provides the functions of two separate gauges through the use of only one single air/fuel ratio gauge 10.

Referring now back to FIGS. 1 and 2, the gauge displays 28 utilized in the present invention may be light emitting diodes (LEDs). Although any number of LEDs may be used, there are preferably eleven LEDs in each set of gauge displays 28. Preferably, the two LEDs 28 are disposed on their respective sides of the gauge controller 18, so as to be spaced apart from each other. This facilitates the visual distinction of the two LEDs 28 apart from each other, so that each of the respective displays may be clearly and conveniently read. Further preferably, although the LEDs 28 may be provided in any fashion on the gauge controller 18, they are disposed on their respective sides of the gauge controller 18 in substantially arcuate configurations (best shown in FIG. 2). It should be recognized herein that other forms of gauge displays 28 (e.g., digital number display, needle meter, etc.) may be used within the gauge 10 of the present invention.

The LEDs 28 are configured to illuminate based on the voltage outputs from the oxygen sensors 20 of the engine. More specifically, as the exhaust gas temperature increases and the sensors reach a temperature where they become active, the LEDs 28 in each set move or illuminate up and down based upon the changes in the voltage outputs. Of course, the illumination of each LED 28 should be bright enough to be seen through the display face 16 if it is tinted.

As such, the LEDs 28 in each set are disposed in a substantially ascending order based upon the voltage ranging from 0 volt to 1 volt. Each LED 28 is operative to illuminate its light when the voltage outputs received from the oxygen sensor(s) 20 generally exceed or match the voltage associated therewith. Preferably, the LEDs 28 in each set are disposed according to the following volt increments:

| Rich-TOP | Volts | Illumination | |
|---|---|---|---|
| LED #11 | 0.901–1.000 | BLUE | |
| LED #10 | 0.801–0.900 | BLUE | (Rich) |
| LED #9 | 0.701–0.800 | BLUE | |
| LED #8 | 0.601–0.700 | GREEN | |
| LED #7 | 0.501–0.600 | GREEN | |
| LED #6 | 0.451–0.500 | GREEN | (Optimal) |
| LED #5 | 0.401–0.450 | GREEN | |
| LED #4 | 0.301–0.400 | GREEN | |
| LED #3 | 0.201–0.300 | RED | |
| LED #2 | 0.101–0.200 | RED | (Lean) |
| LED #1 | 0.000–0.100 | RED | |
| Lean-Bottom | | | |

As seen from the above table, there are three classifications of the exhaust mixtures: Lean, optimal and rich. The LEDs 28 belonging to the lean classification can project out a first colored illumination such as red, whereas the one belonging to the rich classification can project out a second colored illumination such as green. The LEDs 28 in the rich classification provides a third colored illumination such as blue. However, it should be noted that different color scheme may be used other than the ones described herein.

In particular, the LEDs 28 having the voltage in a range from about 0 volt to about 0.3 volt represent a lean exhaust mixture in which the amount of air is substantially greater than the amount of unburned fuel. In the similar concept, the LEDs 28 having the voltage in a range from about 0.301 volt to about 0.7 volt represents a substantially equal amount of air and unburned fuel. This is the preferred exhaust mixture in which the ratio between air and unburned fuel is optimal or stoichiometric at this stage. In addition, the LEDs 28 having the voltage in a range from about 0.701 volt to about 1.0 volt represents an exhaust mixture in which the amount of unburned fuel is substantially greater than the amount of air. Through illuminating certain ones of the LEDs 28, the driver would know the contents, and thus the status, of the exhaust mixture of his or her vehicle.

Referring now to FIGS. 3 and 4, a powertrain control module (PCM) 30 utilizes the oxygen sensor(s) 20 to keep the engine running at the optimal or stoichiometric level when used in a fuel injected application. The PCM 30 is able to do this by continually crossing the rich/lean levels. More particularly, the PCM 30 leans the exhaust mixture for fuel economy until the oxygen sensor(s) 20 senses lean. Upon this occurrence, the PCM 30 then riches the exhaust mixture until the oxygen sensor(S) 20 senses rich. Likewise, the PCM 30 would richen the exhaust mixture for maximum power until the oxygen sensor(s) 20 senses rich in which the PCM would then lean out the exhaust mixture. This loop is typically continued.

Preferably but optionally, at least one auto zeroing circuit 31 may be provided with the air/fuel ratio gauge 10 of the present invention. Essentially, the auto zeroing circuit(s) 31 functions to basically zero the two visual indicator sets 28 at their respective zero levels. By providing such function, the two sets of visual indicators 28 may reflect a zero reading when the respective circuitry is at its sleep state, even if that one sleep state is different from the other sleep state. Since the ratio gauge 10 of the present invention is preferably a digital gauge, the signals may possibly be auto zeroed before they are digitized.

Further preferably but optionally, at least one buffering circuit 33 may be provided with the air/fuel ratio gauge 10 of the present invention. Such buffering circuit(s) 33 would amount to filtering the signal to move it out and remove the jitter. The buffering circuit(s) 33 may presumably be any of a variety of functions that could selectively smooth depending upon the desired characteristics of the present air/fuel ratio gauge 10. Similar to a shock absorber, the buffering circuit(s)/filter(s) 33 may absorb minor oscillations, but react more crisply when the movement is more dramatic. In this respect, the visual effect of the buffering circuit(s)/filter(s) 33 would be that the gauge displays 28 would rise and fall more smoothly, though still responsive to shock changes.

It may be possible that the above-described buffering is adjustable (e.g., for high buffering—high performance/diagnostic uses, for low buffering—urban driving uses). The buffering may be implemented by simply creating a larger dead zone about a current position so that the system responds only when the movement exceeds that dead zone. The term would be to refer to setting a threshold, and modifying the threshold depending upon the desired responsiveness.

Similar to the prior art gauges, the air/fuel ratio gauge 10 of the present invention may further communicate with other components of the vehicle. As one of ordinary skill in the art would appreciate, the air/fuel ratio gauge 10 needs to be electrically connected to other vehicular components in addition to the oxygen sensor(s) 20 in order to be operable. The detailed specifics of such connections will not be repeated herein as it would be obvious to a person of ordinary skilled in the art who is familiar with the designs and/or installations of the air/fuel gauges.

However, it should be pointed out that the air/fuel ratio gauge 10 of the present invention may be electrically connected to the ground 32 and the dash lighting 34 of the vehicle, for example. Further exemplary connection may be its electrical connection to the ignition switch 36 and the engine ground 38 of the vehicle. Some or all of such connections may be selectively employed in conjunction with the use of the present invention's air/fuel ratio gauge 10. It should be indicated that other forms of electrical connections may be necessary and/or made other than what have been described here.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. An air/fuel ratio device for monitoring a first air/fuel ratio of a first exhaust and a second air/fuel ratio of a second exhaust via respective first and second oxygen sensors, the device comprising:
    a gauge housing; and
    a gauge disposed adjacent to the gauge housing and being in electrical communication with the oxygen sensors and operative to receive sensor voltage output signals from the oxygen sensors, the gauge having first and second gauge displays juxtaposed to each other and operative to independently display the received signal of respective first and second oxygen sensors to facilitate simultaneous viewing and comparison of the first and second air/fuel ratios of the first and second exhausts.

2. The device of claim 1 wherein the gauge housing has at least two sensor terminals in communication with the gauge wherein the sensor terminals are operative to communicate the sensor voltage output signals to the gauge.

3. The device of claim 1 wherein each of the gauge displays is operative to display the associated sensor information independent of the other gauge display based upon the sensor voltage output signal received from the associated sensor.

4. The device of claim 1 wherein the sensor voltage output signal ranges from about 0 volt to about 1 volt.

5. The device of claim 4 wherein the sensor voltage output signal in a range from about 0 volt to about 0.3 volt represents a substantially greater amount of air than fuel in the engine exhaust mixture.

6. The device of claim 4 wherein the sensor voltage output signal in a range from about 0.301 volt to about 0.7 volt represents a substantially equal amount of air and fuel in the engine exhaust mixture.

7. The device of claim 4 wherein the sensor voltage output signal in a range from about 0.701 volt to about 1.0 volt represents a substantially greater amount of fuel than air in the engine exhaust mixture.

8. The device of claim 1 wherein the gauge displays include light emitting diodes.

9. The device of claim 1 further comprising at least one auto zeroing circuit operative to zero the gauge displays at zero levels, the auto zeroing circuit being in communication with the gauge.

10. The device of claim 1 further comprising at least one buffering circuit for attenuating transient oscillation of the sensor information displayed by the gauge display, the buffering circuit being in communication with the gauge.

11. An engine system for monitoring a first air/fuel ratio of a first exhaust and a second air/fuel ratio of a second exhaust, the system comprising:
    an engine having first and second oxygen sensors for respectively detecting the first and second air/fuel ratios; and
    an air/fuel ratio device, comprising:
        a gauge housing; and
        a gauge disposed adjacent to the gauge housing and being in electrical communication with the oxygen sensors and operative to receive sensor voltage output signals from the oxygen sensors, the gauge having first and second gauge displays juxtaposed to each other and operative to independently display the received signal of respective first and second oxygen sensors to facilitate simultaneous viewing and comparison of the first and second air/fuel ratios of the first and second exhausts.

12. The system of claim 11 wherein the gauge housing has at least two sensor terminals in communication with the gauge wherein the sensor terminals are operative to communicate the sensor voltage output signals to the gauge.

13. The system of claim 12 wherein each of the gauge displays is operative to display the associated sensor information independent of the other gauge display based upon the sensor voltage output signal received from the associated sensor.

14. The system of claim 11 wherein the sensor voltage output signal ranges from about 0 volt to about 1 volt.

15. The system of claim 14 wherein the sensor voltage output signal in a range from about 0 volt to about 0.3 volt represents a substantially greater amount of air than fuel in the engine exhaust mixture.

16. The system of claim 14 wherein the sensor voltage output signal in a range from about 0.301 volt to about 0.7 volt represents a substantially equal amount of air and fuel in the engine exhaust mixture.

17. The system of claim 14 wherein the sensor voltage output signal in a range from about 0.701 volt to about 1.0 volt represents a substantially greater amount of fuel than air in the engine exhaust mixture.

18. The system of claim 11 wherein the gauge displays include light emitting diodes.

19. The system of claim 11 further comprising at least one auto zeroing circuit operative to zero the gauge displays at zero levels, the auto zeroing circuit being in communication with the gauge.

20. The system of claim 11 further comprising at least one buffering circuit for attenuating transient oscillation of the sensor information displayed by the gauge display, the buffering circuit being in communication with the gauge.

* * * * *